United States Patent [19]

D'Silva

[11] 4,138,423
[45] Feb. 6, 1979

[54] N-DITHIO CARBAMOYL OXIMES

[75] Inventor: Themistocles D. J. D'Silva, South Charleston, W. Va.

[73] Assignee: Union Carbide Corporation, New York, N.Y.

[21] Appl. No.: 701,674

[22] Filed: Jul. 1, 1976

Related U.S. Application Data

[63] Continuation-in-part of Ser. No. 486,632, Jul. 8, 1974, Pat. No. 4,080,469.

[51] Int. Cl.² ............ C07C 69/02; C07C 121/14; A01N 9/12
[52] U.S. Cl. .......... 260/453 RW; 260/465 D; 260/465.4; 260/464; 424/298; 424/327; 560/13; 560/16; 560/118; 560/125; 560/150; 560/153
[58] Field of Search ............... 424/327, 298; 260/453 RW, 465 D, 465.4; 560/13, 16, 125, 150, 153

[56] References Cited

U.S. PATENT DOCUMENTS

| | | | |
|---|---|---|---|
| 3,639,633 | 1/1972 | Buchanan | 424/327 |
| 3,673,236 | 6/1972 | Brechbuhler et al. | 260/465.4 |
| 3,726,908 | 4/1973 | Buchanan | 424/298 |
| 3,812,209 | 5/1974 | Brown | 424/298 |
| 3,939,192 | 2/1976 | Kuhle et al. | 260/453 R |
| 3,960,943 | 6/1976 | Brown et al. | 260/453 RW |
| 3,980,683 | 9/1976 | Isa et al. | 260/533 A X |

FOREIGN PATENT DOCUMENTS 6615725 11/1966 Netherlands ............ 260/453 RW

*Primary Examiner*—Lewis Gotts
*Assistant Examiner*—Robert C. Whittenbaugh
*Attorney, Agent, or Firm*—Robert C. Brown

[57] ABSTRACT

Novel N-dithio carbamoyl oxime compounds have exceptional pesticidal activity.

19 Claims, No Drawings

N-DITHIO CARBAMOYL OXIMES

This application is a continuation-in-part of copending U.S. patent application Ser. No. 486,632, filed July 8, 1974, now U.S. Pat. No. 4,080,469.

This invention relates to carbamate compounds and to their preparation.

More particularly this invention relates to compounds corresponding to the following general formula:

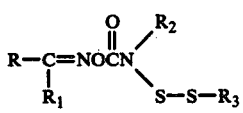

wherein:

R is carbamoyl, lower alkyl, lower alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl, lower phenylalkylsulfonyl, lower alkylcarbamoyl, dilower alkylcarbamoyl or $R_4CON(R_5)$- groups all of which groups may be further substituted with one or more chloro, bromo, fluoro, nitro cyano or amido substituents and the phenyl moieties of said groups may be still further substituted with one or more lower alkyl or lower alkoxy groups;

$R_1$ is hydrogen, chloro, bromo, fluoro, cyano or lower alkyl groups having from 1 to 4 carbon atoms or a lower alkylthio, lower alkoxy, lower carboalkoxyalkylthio or lower alkylthioalkyl group in which any alkyl moiety may be substituted with one or more chloro, bromo, fluoro, cyano, amido or nitro substituents;

$R_2$ is lower alkyl or lower alkyl substituted with one or more chloro, bromo, fluoro, nitro or cyano substituents or phenyl or lower phenyl alkyl either unsubstituted or substituted with one or more chloro, bromo, fluoro, nitro, cyano, lower alkyl or lower alkoxy substituents;

$R_3$ is alkyl, alkenyl, cycloalkyl, bicycloalkyl, cycloalkenyl, bicycloalkenyl, phenyl or phenylalkyl all of which may be either unsubstituted or substituted with one or more chloro, bromo, fluoro, cyano, alkyl, alkoxy or haloalkyl substituents;

$R_4$ and $R_5$ are individually hydrogen or lower alkyl.

These compounds with varying degrees of efficiency are useful in combating insects and mites. In general, the compositions having the greatest degree of pesticidal activity are those in which the combined total number of aliphatic carbon atoms in the substituents R, $R_1$ and $R_2$ does not exceed about 10 carbon atoms.

The preferred compounds of this invention are those in which $R_2$ is alkyl.

It will be appreciated that the compounds of this invention will exist in at least two isomeric forms. In the "syn" configuration, the oxygen atom of the oximino function is on the same side of the oximino double bond as the $R_1$ substituent in the generic formula set forth above while in the "anti" configuration, the oxygen atom is on the opposite side of the oximino function. Both isomers are within the scope of my invention, however, the syn isomers are preferred due to their greater biological activity.

The compounds of this invention in comparison to the corresponding N-methylcarbamate compounds, some of which are well known insecticides, have been found to possess essentially equivalent insecticidal and miticidal activity although in some cases enhanced activity against particular pests have been observed. Surprisingly, however, the compounds of this invention demonstrate a sharp reduction in mamalian toxicity as compared to the N-methyl compounds and a dramatic reduction in phytotoxicity to important economic crops such as cotton, tomatoes, beans and corn which are highly susceptible to phytotoxic injury by certain of the corresponding N-methyl carbamate compounds such as methomyl. In addition nearly all of the compounds of this invention are quite stable under normal conditions and can be stored for long periods of time without appreciable loss or reduction in biological activity. This is to be contrasted with many of the corresponding N-methyl carbamate compounds which are relatively unstable and cannot be stored for any appreciable length of time and as such are not useful pesticides because of practical considerations.

The compounds of this invention can be prepared conveniently in accordance with the following general reaction scheme:

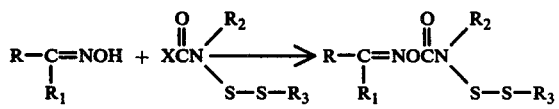

wherein R, $R_1$, $R_2$ and $R_3$ are as described above and where X is either chlorine or fluorine.

The oxime precursors used in the preparation of a compounds of this invention can be prepared by conventional means as for example by the methods described in U.S. Pat. Nos. 3,217,036, 3,217,037, 3,400,153 3,536,760 and 3,576,834.

The carbamoyl halide compounds used in the preparation of the compounds of this invention can be prepared by reacting an appropriately substituted thiosulfenyl chloride with an appropriately substituted carbamoyl fluoride; by the reaction of an appropriately substituted N-chlorothio carbamoyl chloride with an appropriately substituted mercaptan or by the reaction between a substituted thiosulfenylamino compound and phosgene. These reactions are preferably carried out in an aprotic solvent such as toluene, benzene, xylene, dioxane, methylene chloride or the like. These reactions are carried out in the presence of an oganic base, preferably a tertriary amine such as triethylamine. The above enclosed reactions are described in more detail in my copending U.S. patent application Ser. No. 486,631, filed July 8, 1974 entitled Carbamoyl Halide Compositions.

The reaction between the oxime compound and the carbamoyl halide compound is preferably carried out in an aprotic solvent and in the presence of a base. The preferred base materials are tertiary amines and alkaline earth bases. Yields obtained by this reaction are generally quantitative, The following specific examples are presented to more particularly illustrate the manner in which the compounds of this invention may be prepared.

Example I

Preparaton of 1-Methylthioacetaldehyde O-[N-methyl-N-(2-methyl-2-propanethiosulfenyl)carbamoyl]oxime.

To a solution of 2.83 g (0.027 m) of 1-methylthioacetaldoxime and 11.15 g (0.027 m) of N-methyl-N-(2-methyl-2-propanethiosulfenyl)carbamoyl fluoride in 75 ml of dioxane, was added dropwise 2.72 g (0.027 m) of triethylamine. After stirring for 72 hrs. at ambient temperature the reaction mixture was concentrated under reduced pressure, it was diluted with water and extracted with ethyl acetate. The organic extract was washed with water, dried over magnesium sulfate and concentrated. Crystallized from isopropyl ether-hexane solution to afford a white solid — m.p. 67–69° C. On recrystallization. m.p. 71–73° C.

Calc'd for $C_9H_{18}N_2O_2S_3$: C, 38.46; H, 6.40; N, 9.88. Found: C, 38.57; H, 6.20; N, 9.95.

EXAMPLE II

Preparation of 1-Methylthioacetaldehyde O-[N-methyl-N-(cyclohexanethiosulfenyl)carbamoyl]oxime To a suspension of 4.2 g (0.04 m) of 1-methylthioacetaldoxime, 2.6 g (0.04 m) of powdered anhydrous potassium hydroxide and 0.04 g of dicyclohexyl-18-crown-6 in 150 ml of benzene was added 4.64 g (0.04 m) of N-methyl-N-(cyclohexylthiosulfenyl)carbamoyl fluoride. The temperature of the reaction mixture was maintained below 30° C. by external cooling. After stirring for 1.5 hrs. the reaction mixture was diluted with ethyl acetate, washed with water, dried over magnesium sulfate and concentrated under reduced pressure. Chromatographic purification of the residue yielded 2.9 g of m.p. 70–71° C.

Calc'd for $C_{11}H_{20}N_2O_2S_3$: C, 42.83; H, 6.53; N, 9.08. Found: C, 42.84; H, 6.44; N, 9.10.

EXAMPLE III

Preparation of 1-Methylthioacetaldehyde O-[N-methyl-N-(4-chlorophenylthiosulfenyl)carbamoyl]oxime.

To a solution of 3.0 g (0.0286 m) of 1-methylthioacetaldoxime, 7.2 g (0.0286 m) of N-methyl-N-(4-chlorophenylthiosulfenyl)carbamoyl fluoride in 50 ml of diisopropyl ether, was added dropwise 3.89 g (0.0286 m) of triethylamine. The temperature was maintained to about 30° C. by external cooling. After 4 hrs. the solid precipitate was removed by filtration and taken up in ethyl acetate. The organic solution was washed with water, dried and concentrated to afford, after crystallization, 2.6 g of m.p. 71–72° C.

Calc'd for $C_{11}H_{13}ClN_2O_2S_3$: C, 39.27; H, 3.89; N, 8.32. Found: C, 39.21; H, 3.77; N, 8.35.

EXAMPLE IV

Preparation of 1-(2-Cyanoethylthio) acetaldehyde O-[N-methyl-N-isopropylthiosulfenyl)carbamoyl]oxime To a solution of 1.03 g (0.007 m) of 1-(2-cyanoethylthio)acetaldoxime and 1.32 g (0.007 m) of N-methyl-N-(isopropylthiosulfenyl) carbamoyl fluoride in 25 ml of dioxane was added dropwise 0.36 g of triethylamine. After stirring for 48 hrs. at room temperature, the reaction mixture was quenched with 100 ml of water and extracted with 3 × 50 ml of ethyl acetate. The organic layer was washed with water, dried and concentrated. The product was crystallized from isopropyl ether ethyl acetate solution to yield 1.1 g of a white solid. m.p. 74–75° C.

Calc'd for $C_{10}H_{17}N_3O_2S_3$: C, 39.06; H, 5.57; N, 13.67. Found: C, 39.08; H, 5.31; N, 13.61.

EXAMPLE V

Preparation of 2-Methyl-2-methylthiopropionaldehyde O-[N-methyl-N-2-methyl-2-propanethiosulfenyl)carbamoyl]oxime To a solution of 3.0 g (0.0225 m) of 2-methyl 2-methylthiopropionaldoxime and 4.47 g (0.0225 m) of N-methyl-N-(2-methyl-2-propane thiosulfenyl)carbamoyl fluoride in 25 ml of dioxane was added dropwise 2.28 g (0.0225 m) of triethylamine. After stirring for 72 hrs. the mixture was diluted with 150 ml of cold water and extracted in ethylacetate. The organic extract was washed in turn with water, dilute sodium hydroxide, dilute hydrochloric acid and water. It was dried over magnesium sulfate, concentrated to a residual oil. Column chromatography afforded 1.35 g of an oil.

Calc'd for $C_{11}H_{22}N_2O_2S_3$: C, 42.55; H, 7.14; N, 9.02. Found: C, 42.52; H, 7.10; N, 8.57.

EXAMPLE VI

Preparation of 1-Methylthioacetaldehyde O-[N-methyl-N-(methylthiosulfenyl)carbamoyl]oxime.

1-Methylthioacetaldehyde O-[N-methyl-N-(methylthiosulfenyl)carbamoyl]oxime was prepared by the procedure employed in Example I by reacting 3.38 g of 1-methylthioacetaldoxime, 5.0 g of N-methyl-N-(methylthiosulfenyl) carbamoyl fluoride and 3.25 g of triethylamine in 25 ml of dioxane. m.p. 56–57° C.

Calc'd for $C_6H_{12}N_2O_2S_3$: C, 29.98; H, 5.03; N, 11.66. Found: C, 30.03; H, 4.96; N, 11.65.

EXAMPLE VII

Preparation of 1-Methylthioacetaldehyde O-[N-methyl-N-(butylthiosulfenyl)carbamoyl]oxime.

1-Methylthioacetaldehyde O-[N-methyl-N-(butylthiosulfenyl)carbamoyl]oxime was prepared by the procedure employed in Example II by reacting 4.2 g of 1-methylthioacetaldoxime, 7.92 g of N-methyl-N-(butylthiosulfenyl) carbamoyl fluoride, 2.6 g of potassium hydroxide, 0.020 g of crown ether in 100 ml of benzene. Weight of 1-Methylthioacetaldehyde O-[N-methyl-N-(butylthiosulfenyl)carbamoyl]oxime 11.0 g. m.p. 30–31° C.

Calc'd for $C_9H_{18}N_2O_2S_3$: C, 38.27; H, 6.42; N, 9.92. Found: C, 38.22; H, 6.27; N, 9.92.

EXAMPLE VIII

Preparation of 1-Methylthioacetaldehyde O-[N-methyl-N-(octylthiosulfenyl)carbamoyl]oxime.

1-Methylthioacetaldehyde O-[N-methyl-N-(octylthiosulfenyl)carbamoyl] oxime was prepared by the procedure employed in Example I by reacting 2.1 g of 1-methylthioacetaldoxime, 5.07 g of N-methyl-N-(octylthiosulfenyl)carbamoyl fluoride, 2.02 g of triethylamine in 25 ml of dioxane. Weight of the residual oil 6.2 g.

Calc'd for $C_{13}H_{26}N_2O_2S_3$: C, 46.12; H, 7.74; N, 8.28. Found: C, 45.71; H, 7.55; N, 8.29.

EXAMPLE IX

Preparation of 1-Methylthioacetaldehyde O-[N-methyl-N-(phenylthiosulfenyl)carbamoyl]oxime.

1-Methylthioacetaldehyde O-[N-methyl-N-(phenylthiosulfenyl)carbamoyl]oxime was prepared by the procedure employed in Example I by reacting 5.0 g (0.0477 m) of 1-methylthioacetaldoxime with 10.35 g (0.0477 m) of N-methyl-N-(phenylthiosulfenyl)carbamoyl fluoride and 4.83 g (0.0477 m) of triethylamine in 75 ml of dioxane. Weight of the residual oil 6.18 g. Infrared 5.73μ (c=o). NMR, δ2.19 (S, 3H, CH$_3$); 2.28 (S, 3H, CH$_{3S}$), 3.18 (5, 3H, CH$_3$N), 7.2–7.8 (m, 5H, aromatic).

Calc'd for $C_{11}H_{14}N_2O_2S_3$: C, 43.68; H, 4.67; N, 9.26. Found: C, 41.63; H, 4.40; N, 8.63.

EXAMPLE X

1-Methylthioacetaldehyde O-[N-methyl-N-(4-methyl phenylthiosulfenyl)carbamoyl]oxime.

1-Methylthioacetaldehyde O-[N-methyl-N-(4-methylphenylthiosulfenyl)carbamoyl]oxime was prepared by the procedure employed in Example I by reacting 3.0 g (0.0286 m) of 1-methylthioacetaldoxime with 6.61 g (0.0286 m) of N-methyl-N-(4-methylphenylthiosulfenyl) carbamoyl fluoride and 2.89 g (0.0286 m) of triethylamine in 50 ml of dioxane. Weight of 1-methylthioacetaldehyde O-[N-methyl-N-(4-methylphenylthiosulfenyl)carbamoyl]oxime 5.2 g. m.p. 79–80° C.

Calc'd for $C_{12}H_{16}N_2O_2S_3$: C, 45.54; H, 5.10; N, 8.85. Found: C, 45.38; H, 4.98; N, 8.83.

EXAMPLE XI

Preparation of 1-methylthioacetaldehyde O-N-methyl-N-(4-t-butylphenylthiosulfenyl)carbamoyl]oxime.

1-Methylthioacetaldehyde O-N-methyl-N-(4-t-butylphenylthiosulfenyl)carbamoyl] oxime was prepared by the procedure employed in Example I by reacting 0.766 g (0.0073 m) of 1-methylthioacetaldoxime with 2.0 g (0.0073 m) of N-methyl-N-(4-t-butylphenylthiosulfenyl) carbamoyl fluoride and 0.736 g (0.0073 m) of triethylamine in 25 ml of dioxane. Weight of 1-Methylthioacetaldehyde O-N-methyl-N-(4-t-butylphenylthiosulfenyl)carbamoyl] oxime 1.5 g. m.p. 67–68° C.

Calc'd for $C_{15}H_{22}N_2O_2S_3$: C, 50.24; H, 6.19; N, 7.81. Found: C, 50.17; H, 6.54; N, 7.85.

EXAMPLE XII

Preparation of 1-Isopropylthioacetaldehyde O-N-methyl-N-(2-methyl-2-propanethiosulfenyl)carbamoyl] oxime, was prepared by the procedure employed in Example I, by reacting 2.08 g (0.0157 m) of 1-isopropylthioacetaldoxime with 6.69 g (0.0157 m) of a 50 percent solution of N-methyl-N-(2-methyl-2-propanethiosulfenyl)carbamoyl fluoride and 1.58 g (0.0157 m) of triethylamine in 50 ml of dioxane. Weight of 1-Isopropylthioacetaldehyde O-[N-methyl-N-(2-methyl-2-propanethiosulfenyl)carbamoyl] oxime was 0.4 g as an oil.

Calc'd for $C_{11}H_{22}N_2O_2S_3$: C, 42.55; H, 7.14; N, 9.02. Found: C, 43.33; H, 7.06; N, 8.49.

EXAMPLE XIII

Preparation of 1-(2-Cyanoethylthio)acetaldehyde O-N-methyl-N-2-methyl-2-propanethiosulfenyl)carbamoyl] oxime.

1-(2-Cyanoethylthio)acetaldehyde O-N-methyl-N-(2-methyl-2-propanethiosulfenyl)carbamoyl] oxime was prepared by the procedure employed in Example I, by reacting 2.88 g (0.02 m) of 1-(2-cyanoethylthio)acetaldoxime with 3.94 g (0.02 m) of N-methyl-N-(2-methyl-2-propanethiosulfenyl)carbamoyl fluoride and 2.02 g (0.02 m) of triethylamine in 25 ml of dioxane. Weight of 1-(2-cyanoethylthio)acetaldehyde O-N-methyl-N-2-methyl-2-propanethiosulfenyl)carbamoyl] oxime was 4.5 g. Crystallized from isopropylether. m.p. 90–92° C.

Calc'd for $C_{11}H_{19}N_3O_2S_3$: C, 41.09; H, 5.96; N, 13.07. Found: C, 40.85; H, 5.92; N, 13.01.

EXAMPLE XIV

Preparation of 2-Methyl-2-methylthiopropionaldehyde O-N-methyl-N-(4chlorophenylthiosulfenyl)carbamoyl] oxime.

2-Methyl-2-methylthiopropionaldehyde O-N-methyl-N-(4-chlorophenylthiosulfenyl)carbamoyl] oxime was prepared by the procedure employed in Example I by reacting 4.0 g (0.03 m) of 2-methyl-2-methylthiopropionaldoxime with 7.55 g (0.03 m) of N-methyl-N-(4-chlorophenylthiosulfenyl)carbamoyl fluoride and 3.07 g (0.03 m) of triethylamine in 50 ml of dioxane. Weight of 2-methyl-2-methylthiopropionaldehyde O-N-methyl-N-(4-chlorophenylthiosulfenyl)carbamoyl] oxime was 2.87 g. m.p. 70–72° C.

Calc'd for $C_{13}H_{17}ClN_2O_2S_3$: C, 42.78; H, 4.70; N, 7.68. Found: C, 42.79; H, 4.61; N, 7.66.

EXAMPLE XV

Preparation of 1-Methylthioacetaldehyde O-N-methyl-N-(isopropylthiosulfenyl)carbamoyl] oxime.

1-Methylthioacetaldehyde O-N-methyl-N-(isopropylthiosulfenyl)carbamoyl] oxime was prepared by the procedure employed in Example II, by reacting 5.0 g (0.0476 m) of 1-methylthioacetaldoxime with 8.93 g (0.0476 m) of N-methyl-N-(isopropylthiosulfenyl)carbamoyl fluoride and 3.1 g (0.0476 m) of potassium hydroxide, 0.02 g of dicyclohexyl-18-crown-6 in 100 ml of benzene. Weight of 1-methylthioacetaldehyde O-N-methyl-N-(isopropylthiosulfenyl)carbamoyl]oxime was 5.8 g. m.p. 54–56° C.

Calc'd for $C_8H_{16}N_2O_2S_3$: C, 35.79; H, 6.01; N, 10.44. Found: C, 35.63; H, 5.94; N, 10.40.

EXAMPLE XVI

Preparation of 1-Methylthioacetaldehyde O-N-methyl-N-(t-octylthiosulfenyl)carbamoyl] oxime.

1-Methylthioacetaldehyde O-N-methyl-N-(t-octylthiosulfenyl)carbamoyl] oxime was prepared by the procedure employed in Example II, by reacting 2.1 g (0.02 m) of 1-methylthioacetaldoxime with 5.06 g (0.02 m) of N-methyl-N-(t-octylthiosulfenyl)carbamoyl fluoride in the presence of 1.3 g (0.02 m) of potassium hydroxide and 0.02 g of dicyclohexyl-18-crown-6 in 60 ml of benzene.

Weight of 1-methylthioacetaldehyde O-N-methyl-N-(t-octylthiosulfenyl)carbamoyl] oxime was 5.0 g. $N_D^{23}$ 1.42 35.

Calc'd for $C_{13}H_{26}N_2O_2S_3$: C, 46.12; H, 7.74; N, 8.27.
Found: C, 46.71; H, 7.50; N, 8.12.

EXAMPLE XVII

Preparation of 2-Methyl-2-nitropropionaldehyde O-N-methyl-N-(4-methylphenylthiosulfenyl)carbamoyl] oxime.

2-Methyl-2-nitropropionaldehyde O-N-methyl-N-(4-methylphenylthiosulfenyl)carbamoyl] oxime was prepared by the procedure employed in Example I by reacting 5.0 g (0.038 m) of 2-methyl-2-nitropropionaldoxime with 8.79 g (0.038 m) of n-methyl-N-(4-methylphenylthiosulfenyl)carbamoyl fluoride in the presence of 3.84 g (0.038 m) of triethylamine in 100 ml of toluene. After chromatographic purification 3.0 g of the white solids was isolated. m.p. 61.5–63° C.

Calc'd for $C_{13}H_{17}N_3O_4S_2$: C, 45.46; H, 4.99; N, 12.24.
Found: C, 45.29; H, 4.86; N, 12.15.

EXAMPLE XVIII

Preparation of N-Methyl-N(2-Methyl-2-Propanethiosulfenyl) Carbamoyl Fluoride

To a solution of 231.08 N-methylcarbamoyl fluoride, in 600 ml toluene, cooled to 0° C was added 478.0 g 2-methyl-2-propanethiosulfenyl chloride dissolved in 1000 ml toluene. This was followed by dropwise addition of 303.0 g triethylamine in 1000 ml of toluene. Stirring was continued for an additional 2 hrs. at 5° C. The precipitated salt was filtered off the filtrate concentrated. Wt. of reddish oil 577.0 g. b.p. 75–80° C/0.5 Torr. $N_D^{22}$ 1.4983.

IR(Neat) 5.6 (C=O), 6.9, 7.7, 8.65, 9.25, 9.4 (sh), 10.62 and 13.4μ.

NMR(CDCL$_3$)δ1.4, (S), 9H, t-Bu; 3.23 (d), J=1.0H$_z$, 3H, CH$_3$N.

EXAMPLE XIX

Preparation of N-Methyl-N(4-t-Butylphenylthiosulfenyl) Carbamoyl Fluoride

To a solution of 5.5 g hydrogen fluoride in toluene cooled to −65° C was added dropwise with stirring 15.0 ml of methylisocyanate over a period of 20 minutes after stirring for 1.5 hr. freshly prepared 4-t-butylphenylthiosulfenyl chloride (prepared from 36.2 g 4-t-butylphenol and 31.0 g sulfur dichloride in 800 ml ethyl ether) was added at −10 to 0° C over a period of 0.5 hr. After stirring overnight at ambient temperature, the salt was removed by filtration and the filtrate distilled. b.p. 122–127° C/0.2 Torr.

IR(Neat) 5.6 (C=O) and other import peaks at 7.7, 9.3, 10.55, 12.12 and 13.4μ.

NMR(CDCl$_3$)δ1.27, (S), 9H; 3.15, (d) J=1.0H$_z$, 3H, 7.3–7.6 (m), 4H.

EXAMPLE XX

Preparation of N-Methyl-N(2,4-Dichlorophenylthiosulfenyl)-Carbamoyl Fluoride

An essentially equimolar amont of N-methyl-N-chlorosulfenylcarbamoyl fluoride in toluene solvent is added to 2,4-dichlorophenylthiol followed by dropwise addition of triethylamine, with stirring, until the reaction is complete. The product is separated and purified by the procedures described above.

EXAMPLE XXI

Preparation of N-Allyl-N(Butylthiosulfenyl)Carbamoyl Chloride

An essentially equimolar amount of allyl amine and an equimolar amount of triethylamine is added slowly with stirring to a quantity of butyldithiochloride in toluene until the reaction is complete. The resulting salt precipitate is removed by filtration. An equimolar amount of triethylamine base is then added to the filtrate followed by the slow addition of phosgene until the reaction is complete. The resulting N-Allyl-N-(butylthiosulfenyl)carbamoyl chloride product is separated and purified by the procedure described above. The following compositions in addition to those described in the above examples are illustrative of the new compositions of this invention:

1-Methylthioacetaldehyde-O-[N-methyl-N-methylthiosulfenylcarbamoyl]oxime
1-Methylthioacetaldehyde-O-[N-methyl-N-2-propanethiosulfenyl)carbamoyl]oxime
1-Isopropylthioacetaldehyde-O-[N-methyl-N-butanethiosulfenylcarbamoyl]oxime
1-(2-cyanoethylthio)acetaldehyde-O-[N-methyl-N-octadecanethiosulfenylcarbamoyl]oxime
1-(3-nitroethylthio)propionaldehyde-O-[N-methyl-N-(2-(2-methylpropane)thiosulfenyl)carbamoyl]oxime
1-(methylthioethylthio)acetaldehyde-O-[N-methyl-N-methylthiosulfenylcarbamoyl]oxime
1-Methylthioacetaldehyde-O-[N-methyl-N-(4-chlorophenylthiosulfenyl)carbamoyl]oxime
1-Methylthioacetaldehyde-O-[N-methyl-N-(4-nitrophenylthiosulfenyl)carbamoyl]oxime
1-Methylthioacetaldehyde-O-[N-methyl-N-(3-trifluoromethylphenylthiosulfenyl)carbamoyl]oxime
1-Methylthioacetaldehyde-O-[N-methyl-N-(4-methylphenylthiosulfenyl)carbamoyl]oxime
1-Methylthioacetaldehyde-O-[N-methyl-N-(3,4-dimethylphenylthiosulfenyl)carbamoyl]oxime
1-[Ethoxycarbamoylmethylthio]acetaldehyde-O-[N-methyl-N-(4-chlorophenylthiosulfenyl)carbamoyl]oxime
1-[N-methylacetamidomethylthio]acetaldehyde-O-[N-methyl-N-2(2-methylpropanethiosulfenyl)carbamoyl]oxime
1-Methylthioacetaldehyde-O-[N-phenyl-N-methanethiosulfenylcarbamoyl]oxime
1-Methylthioacetaldehyde-O-[N-chloroethyl-N-methanethiosulfenylcarbamoyl]oxime
1-Methylthioacetaldehyde-O-[N-p-chlorophenyl-N-propanethiosulfenylcarbamoyl]oxime
Bis-methylthioformaldehyde-O-[N-methyl-N-cyclohexanethiosulfenylcarbamoyl]oxime
(2-cyanoethylthio)methylthioformaldehyde-O-[N-methyl-N-butanethiosulfenylcarbamoyl]oxime
1-Methylthioacetaldehyde-O-[N-methyl-N-(2-(2-methylpropane)thiosulfenyl)carbamoyl]oxime
1-(2-propylthio)acetaldehyde-O-[N-methyl-N-(2-(2-methylpropane)thiosulfenyl)carbamoyl]oxime
1-(2-cyanoethylthio)acetaldehyde-O-[N-methyl-N-(2-(2-methylpropane)thiosulfenyl)carbamoyl]oxime
1-Methylthioacetaldehyde-O-[N-methyl-N-(4-t-butylphenylthiosulfenyl)carbamoyl]oxime
1-Methylthioacetaldehyde-O-[N-methyl-N-(2-(2-methylpropane)thiosulfenyl)carbamoyl]oxime
2-Methyl-2-nitropropionaldehyde-O-[N-methyl-N-(2-(2-methylpropane)thiosulfenyl)carbamoyl]oxime 3-Methyl-3-nitrobutanone-2-O-[N-methyl-N-ethanethiosulfenylcarbamoyl]oxime
2-Methyl-2-cyanopropionaldehyde-O-[N-methyl-N-methanethiosulfenylcarbamoyl]oxime
2-Methyl-2-cyanopropionaldehyde-O-[N-methyl-N-octylthiosulfenylcarbamoyl]oxime
2-Methyl-2-cyanopropionaldehyde-O-[N-methyl-N-(2(2-methylpropane)thiosulfenyl)carbamoyl]oxime
2-Methyl-2-nitropropionaldehyde-O-[N-methyl-N-(4-t-butylphenylthiosulfenyl)carbamoyl]oxime
2-Methyl-2-formamidopropionaldehyde-O-[N-methyl-N-butanethiosulfenylcarbamoyl]oxime
2-Methyl-2-acetamidopropionaldehyde-O-[N-methyl-N-(2-(2-methylpropane)thiosulfenyl)carbamoyl]oxime
3-Methyl-3-acetamidobutanone-2-O-[N-methyl-N-octylthiosulfenylcarbamoyl]oxime
2-Methyl-2-methoxypropionaldehyde-O-[N-methyl-N-dodecylthiosulfenyl)carbamoyl]oxime
2-Methyl-2-(1-ethoxycarbonylethylthio)propionaldehyde-O-[N-methyl-N-methanesulfenylcarbamoyl]oxime
2-Methyl-2-methylthiopropionaldehyde-O-[N-methyl-N-(2-(2-methylpropane)thiosulfenyl)carbamoyl]oxime
2-Methyl-2-methylsulfinylpropionaldehyde-O-[N-methyl-N-octylthiosulfenylcarbamoyl]oxime
2-Methyl-2-methylthiopropionaldehyde-O-[N-methyl-N-(4-t-butylphenylthiosulfenyl)carbamoyl]oxime
2-Methyl-2-methylthiopropionaldehyde-O-[N-methyl-N-(4-chlorophenylthiosulfenyl)carbamoyl]oxime
2-Methyl-2-(4-chlorophenylthio)propionaldehyde-O-[N-methyl-N-methanethiosulfenyl carbamoyl]oxime
3,3-Dimethyl-1-methylthiobutanone-2-O-[N-methyl-N-methanethiosulfenylcarbamoyl]oxime
3,3-Dimethyl-1-methylthiobutanone-2-O-[N-methyl-N-(2-(2-methylpropane)thiosulfenyl)carbamoyl]oxime
1,2,2-Tris-(methylthio)propionaldehyde-O-[N-methyl-N-methanethiosulfenylcarbamoyl]oxime
2-Methyl-1,2-bis(methylthio)propionaldehyde-O-[N-methyl-N-octanethiosulfenylcarbamoyl]oxime
2-Methyl-2-methoxy-1-chloropropionaldehyde-O-[N-methyl-N-(2(2-methylpropane)thiosulfenyl)carbamoyl]oxime
2-Methyl-1-2-dicyanopropionaldehyde-O-[N-methyl-N-(2(2-methylpropane)thiosulfenyl)carbamoyl]oxime
2-Methyl-2-cyano-1-methylthiopropionaldehyde-O-[N-methyl-N-octadicanethiosulfenylcarbamoyl]oxime
2-Methyl-2-cyano-1-(2-cyanoethylthio)propionaldehyde-O-[N-methyl-N-methanethiosulfenylcarbamoyl]oxime
2-Methyl-2-nitro-1-(2-cyanoethylthio)propionaldehyde-O-[N-methyl-N-(2(2-methylpropane)thiosulfenyl)carbamoyl]oxime
2-(Methylthiomethyl)-2-methylthiopropionaldehyde-O-[N-methyl-N-(2-(2-methylpropane)thiosulfenyl)carbamoyl]oxime
2-(Ethoxymethyl)-2-methylthiopropionaldehyde-O-[N-methyl-N-butanethiosulfenylcarbamoyl]oxime
2-Methyl-2-methylsulfonylpropionaldehyde-O-[N-methyl-N-methanethiosulfenylcarbamoyl]oxime
Methylthiochloroformaldehyde-O-[N-methyl-N-(2(2-methylpropane)thiosulfenyl)carbamoyl]oxime
2-Cyanoethylthiochloroformaldehyde-O-[N-methyl-N-methylthiosulfenyl carbamoyl]oxime
Bis-methylthioformaldehyde-O-[N-methyl-N-(2-(2-methylpropane)thiosulfenyl)carbamoyl]oxime
(Benzylthio)methylthioformaldehyde-O-[N-methyl-N-pentanetriosulfenylcarbamoyl]oxime
(Methoxy)methylthioformaldehyde-O-[N-methyl-N-octanethiosulfenylcarbamoyl]oxime
Allylthiochloroformaldehyde-O-[N-methyl-N-methanethiosulfenylcarbamoyl]oxime
Bis-methylthioformaldehyde-O-[N-methyl-N-(3-trifluoromethylphenylthiosulfenyl)carbamoyl]oxime Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65–70° F. and 50–70 per cent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5° percent relative humidity, were the test organisms. Infested leaves from a stock culture were placed on the primary leaves of two bean plants six to eight inches in height, growing in a two- and-a-half inch clay pot. 150–200 mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:

A = excellent control
B = partial control
C = no control
Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I
BIOLOGICAL DATA

| Example No. | Structure | Aphid | Mite | Southern Army-worm | Mexican Bean-beetle | Housefly | A.O. Rat. (mg/kg) |
|---|---|---|---|---|---|---|---|
| I | CH₃-C(SCH₃)=NOC(O)N(CH₃)-S-S-C(CH₃)₃ | A | B | A | A | A | 143 |
| II | CH₃-C(SCH₃)=NOC(O)N(CH₃)-S-S-cyclohexyl | A | B | A | A | A | 101 |
| III | CH₃-C(SCH₃)=NOC(O)N(CH₃)-S-S-C₆H₄-Cl | A | A | A | A | A | 160 |
| IV | CH₃-C(SCH₂CH₂CN)=NOC(O)N(CH₃)-S-S-CH(CH₃)₂ | A | A | A | A | A | 14.1 |
| V | CH₃S-C(CH₃)(H)-C(CH₃)=NOC(O)N(CH₃)-S-S-C(CH₃)₃ | A | A | B | A | A | — |
| VI | CH₃-C(SCH₃)=NOC(O)N(CH₃)-S-S-CH₃ | A | B | A | A | A | — |
| VII | CH₃-C(SCH₃)=NOC(O)N(CH₃)-S-S-C₄H₉ | A | B | A | A | A | — |
| VIII | CH₃-C(SCH₃)=NOC(O)N(CH₃)-S-S-C₈H₁₇ | A | A | A | A | A | — |
| IX | CH₃-C(SCH₃)=NOC(O)N(CH₃)-S-S-C₆H₅ | A | B | A | A | A | 143 |
| X | CH₃-C(SCH₃)=NOC(O)N(CH₃)-S-S-C₆H₄-CH₃ | A | B | A | A | A | 63.5 |
| XI | CH₃-C(SCH₃)=NOC(O)N(CH₃)-S-S-C₆H₄-C(CH₃)₃ | A | B | A | A | A | 180 |
| XII | CH₃-C(SCH(CH₃)₂)=NOC(O)N(CH₃)-S-S-C(CH₃)₃ | A | A | A | A | A | 30.8 |
| XIII | CH₃-C(SCH₂CH₂CN)=NOC(O)N(CH₃)-S-S-C(CH₃)₃ | A | A | A | A | A | 10 |

TABLE I-continued
BIOLOGICAL DATA

| Example No. | Structure | Aphid | Mite | Southern Army-worm | Mexican Bean-beetle | Housefly | A.O. Rat. (mg/kg) |
|---|---|---|---|---|---|---|---|
| XIV | $CH_3S-\underset{\underset{CH_3}{\mid}}{\overset{\overset{CH_3}{\mid}}{C}}-\underset{H}{\overset{}{C}}=NO\overset{O}{\overset{\|}{C}}N\overset{CH_3}{\diagdown}_{S-S-\langle\bigcirc\rangle-Cl}$ | A | A | B | A | A | 2 |
| XV | $CH_3-\underset{SCH_3}{\overset{}{C}}=NO\overset{O}{\overset{\|}{C}}N\overset{CH_3}{\diagdown}_{S-S-CH\overset{CH_3}{\diagdown}_{CH_3}}$ | A | A | A | A | A | 113 |
| XVI | $CH_3-\underset{SCH_3}{\overset{}{C}}=NO\overset{O}{\overset{\|}{C}}N\overset{CH_3}{\diagdown}_{S-S-\underset{CH_3}{\overset{CH_3}{\mid}}{C}-CH_2-\underset{CH_3}{\overset{CH_3}{\mid}}{C}CH_3}$ | A | B | A | A | A | — |
| XVII | $O_2N-\underset{CH_3}{\overset{\overset{CH_3}{\mid}}{C}}-\underset{H}{\overset{}{C}}=NO\overset{O}{\overset{\|}{C}}N\overset{CH_3}{\diagdown}_{S-S-\langle\bigcirc\rangle-CH_3}$ | A | A | A | A | A |  |

At higher dosage rates all of the above compositions may be expected to exhibit some activity against the various test species, however the data presented in Table I above clearly indicates a rather high degree of selectivity for some compositions and a broad spectrum of activity for others.

It will be understood that the insect species employed in the above tests are merely representative of a wide variety of pests that can be controlled by use of my compounds. These compounds demonstrate systemic as well as contact toxicity against insects and mites.

It should be noted that in addition to their insecticidal and miticidal activity, noteworthy nematocidal activity was also displayed by our compounds. Comparison tests were conducted to assess the biological and chemical properties of certain representative species of the claimed invention in relation to methomyl, a corresponding N-methyl carbamate composition. The test procedures described above were employed in these experiments in order to determine the $LD_{50}$ (number of parts per million of active ingredients required to achieve fifty percent mortality of the insects tested) for each of the compositions tested. The results of these experiments are set forth in Table II below.

the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash if off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or

TABLE II
COMPARATIVE BIOLOGICAL ACTIVITY $$CH_3-\underset{X}{\overset{}{C}}=NO\overset{O}{\overset{\|}{C}}N\overset{CH_3}{\diagdown}_R$$

| Compound | R | X | Aphid | Mite | Army-worm | Beetle | Fly | Rat |
|---|---|---|---|---|---|---|---|---|
| Methomyl | H | —SCH | 4 | >500 | 11 | 70 | 4 | 48 |
| Example II | —S—S—C(CH$_3$) | —SCH$_3$ | 1.3 | >500 | 6 | 40 | 4 | 143 |
| Example III | —S—S—C(CH$_3$)$_3$ | —SCH(CH$_3$)$_2$ | 9 | 125 | 35 | 31 | 42 | 30.8 |

The compounds contemplated in this invention may be applied as insecticides, miticides and nematocides according to methods known to those skilled in the art. Pesticidal compositions containing the compounds as granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The requuired amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼to 15 pound of active toxicant per acre.

The pesticides contemplated herein prevent attack by insects nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. Compounds of the formula:

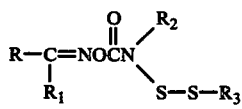

wherein:

R is carbamoyl, lower alkyl, lower alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylsulfonyl, lower alkylcarbamoyl, dilower alkylcarbamoyl or $R_4CON(R_5)$- groups all of which groups may be further substituted with one or more chloro, bromo, fluoro, nitro, cyano or amido substituents and the phenyl moieties of said groups may be still further substituted with one or more lower alkyl or lower alkoxy groups;

$R_1$ is hydrogen, chloro, bromo, fluoro, cyano or a lower alkyl group having from 1 to 4 carbon atoms or a lower alkylthio, lower alkoxy, lower carboalkoxyalkylthio or lower alkylthioalkyl group in which any alkyl moiety may be substituted with one or more chloro, bromo, fluoro, cyano, amido or nitro substituents;

$R_2$ is lower alkyl or lower alkyl substituted with one or more chloro, bromo, fluoro, nitro or cyano substituents or phenyl or lower phenyl alkyl, either unsubstituted or substituted with one or more chloro, bromo, fluoro, nitro, cyano, lower alkyl or lower alkoxy substituents;

$R_3$ is alkyl, alkenyl, cycloalkyl, bicycloalkyl, cycloalkenyl, bicycloalkenyl or phenyl or lower phenylalkyl either unsubstituted or substituted with one or more chloro, bromo, fluoro, nitro, cyano, lower alkyl, lower alkoxy or lower haloalkyl substituents;

$R_4$ and $R_5$ are individually hydrogen or lower alkyl;

2. A compound in accordance with claim 1 wherein the total number of aliphatic carbon atoms included in R, $R_1$ and $R_2$ does not exceed 10 carbon atoms.

3. A compound in accordance with claim 1 in which $R_3$ is alkyl or substituted or unsubstituted phenyl.

4. A compound in accordance with claim 1 in which $R_2$ is alkyl.

5. A compound in accordance with claim 1 in which $R_2$ is methyl.

6. A compound in accordance with claim 1 in which R is alkylthio.

7. A compound in accordance with claim 1 in which R is alkyl.

8. A compound in accordance with claim 1 in which $R_1$ is alkyl.

9. A compound in accordance with claim 1 in which $R_1$ is substituted alkyl.

10. A compound in accordance with claim 1 in which $R_1$ is alkylthio.

11. A compound in accordance with claim 1 in which R, $R_2$ and $R_3$ are alkyl and $R_1$ is alkylthio.

12. A compound in accordance with claim 1 in which R, $R_2$ and $R_3$ are alkyl and $R_1$ is substituted alkylthio.

13. Methylthioacetaldehyde O-[N-methyl-N-2(2-methylpropanethiosulfenyl)-carbamoyl]oxime.

14. 1-Isopropylthioacetaldehyde O-[N-methyl-N-2(2-methylpropanethiosulfenyl)carbamoyl]oxime.

15. Methylthioacetaldehyde O-[N-methyl-N-(4-t-butylphenylthiosulfenyl)carbamoyl]oxime.

16. Methylthioacetaldehyde O-(N-methyl-N-octyl-thiosulfenylcarbamoyl)oxime.

17. 2-Cyanoethylthioacetaldehyde O-[N-methyl-N-2(2-methylpropanethiosulfenyl)carbampyl]oxime.

18. A compound of the formula:

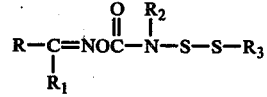

wherein

R, $R_2$ and $R_3$ are alkyl;

$R_1$ is alkylthio or alkylthio substituted with one or more chloro, bromo, fluoro, amido or nitro groups.

19. Compounds of the formula:

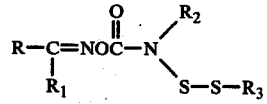

wherein:

R is carbamoyl, lower alkyl, lower alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylsulfonyl, lower alkylcarbamoyl, dilower alkylcarbamoyl, or $R_4CON(R_5)$- groups, all of which groups may be further substituted with one or more chloro, bromo, fluoro, nitro or amido substituents and the phenyl moieties of said groups may be still further substituted with one or more lower alkyl or alkoxy groups;

$R_1$ is hydrogen, chloro, bromo, fluoro or a lower alkyl group having from 1 to 4 carbon atoms or a lower alkylthio, lower alkoxy, lower carboalkoxyalkylthio or lower alkylthioalkyl group in which any alkyl moiety may be substituted with one or more chloro, bromo, fluoro, amido or nitro groups;

$R_2$ is lower alkyl or lower alkyl substituted with one or more chloro, bromo, fluoro, or nitro groups or either substituted or unsubstituted phenyl or lower phenylalkyl wherein the permissible substituents are one or more chloro, bromo, fluoro, nitro, lower alkyl or lower alkoxy groups;

$R_3$ is alkyl, alkenyl, cycloalkyl, bicycloalkyl, cycloalkenyl, bicycloalkenyl, phenyl or phenylalkyl, all of which may be either unsubstituted or substituted with one or more chloro, bromo, fluoro, cyano, alkyl, alkoxy or haloalkyl groups;

$R_4$ and $R_5$ are individually hydrogen or lower alkyl.

* * * * *

UNITED STATES PATENT AND TRADEMARK OFFICE
CERTIFICATE OF CORRECTION

PATENT NO. : 4,138,423
DATED : February 6, 1979
INVENTOR(S) : T. D. J. D'Silva

It is certified that error appears in the above—identified patent and that said Letters Patent are hereby corrected as shown below:

Column 16, line 45, "if" should read --it--; line 58, Table II under X, "-SCH" should read -- -SCH$_3$--; line 59, Table II under R, "-S-S-C(CH$_3$)" should read -- -S-S-C(CH$_3$)$_3$--. Column 17, line 3, "requuired" should read --required--. Column 18, line 38, "carbampyl" should read --carbamoyl--.

Signed and Sealed this

Nineteenth Day of June 1979

[SEAL]

Attest:

RUTH C. MASON
*Attesting Officer*

DONALD W. BANNER
*Commissioner of Patents and Trademarks*